United States Patent [19]

Jiang

[11] Patent Number: 5,483,009
[45] Date of Patent: Jan. 9, 1996

[54] POLYMER DERIVED FROM CYCLIC AMIDE AND MEDICAL DEVICES MANUFACTURED THEREFROM

[75] Inventor: Ying Jiang, North Haven, Conn.

[73] Assignee: United States Surgical Corporation, Norwalk, Conn.

[21] Appl. No.: 423,171

[22] Filed: Apr. 18, 1995

Related U.S. Application Data

[62] Division of Ser. No. 255,692, Jun. 9, 1994, Pat. No. 5,446,108, which is a division of Ser. No. 9,122, Jan. 26, 1993, Pat. No. 5,349,045.

[51] Int. Cl.$^6$ .................. C08F 267/10; C08G 69/14; A61B 19/00
[52] U.S. Cl. .......... 525/417; 128/898; 528/310; 528/321; 528/323; 528/332; 528/354; 528/367; 606/139; 606/146; 606/148; 606/228; 606/230
[58] Field of Search .................. 525/417; 528/310, 528/321, 323, 332, 354, 367; 128/898; 606/139, 146, 148, 228, 230

[56] References Cited

U.S. PATENT DOCUMENTS

| | | | |
|---|---|---|---|
| 2,146,210 | 2/1939 | Graves | 528/332 |
| 3,133,048 | 5/1964 | Moore et al. | |
| 3,445,441 | 5/1969 | Rushton | 528/332 |
| 3,509,106 | 4/1970 | Lotz et al. | |
| 3,773,739 | 11/1973 | Bonvicini et al. | 528/332 |
| 4,064,086 | 12/1977 | Cowsar et al. | 524/601 |
| 4,126,614 | 11/1978 | Suzuki | 540/454 |
| 4,343,931 | 8/1982 | Barrows | 528/291 |
| 4,713,437 | 12/1987 | Pilz et al. | 528/336 |
| 4,855,397 | 8/1989 | Barbee et al. | 528/335 |
| 5,051,491 | 9/1991 | Pipper et al. | 528/335 |
| 5,068,220 | 11/1991 | Vanderbilt et al. | 514/3 |
| 5,086,162 | 2/1992 | Speranza et al. | 528/339 |
| 5,118,785 | 6/1992 | Speranza et al. | 528/347 |

FOREIGN PATENT DOCUMENTS 1195317  6/1965  Germany.

*Primary Examiner*—Shelley A. Dodson

[57] ABSTRACT

A moldable and/or extrudable polymer which is useful for the manufacture of surgical devices such as sutures, staples, clips, etc., possesses structural units derived from a cyclic amide monomer containing oxygen, sulfur or nitrogen in the ring.

2 Claims, 1 Drawing Sheet

POLYMER DERIVED FROM CYCLIC AMIDE AND MEDICAL DEVICES MANUFACTURED THEREFROM

This is a divisional of U.S. application Ser. No. 08/255,692 filed Jun. 9, 1994, now U.S. Pat. No. 5,446,108, which is a divisional of of U.S. application Ser. No. 08/009,122 filed Jan. 26, 1993, now U.S. Pat. No. 5,349,045.

BACKGROUND OF THE INVENTION

This invention relates to a moldable and/or extrudable polymer possessing structural units derived from certain hetero oxygen, sulfur or nitrogen-containing cyclic amide monomers and to surgical devices such as staples, clips, sutures, pins, screws, prosthetic devices, hernial repair meshes, growth matrices, drug delivery devices, anastomosis rings, etc., manufactured from the polymer.

U.S. Pat. No. 3,173,048 discloses a 6-membered ring compound, referred to as a 3-morpholinone, containing an amide linkage and a hetero oxygen atom. Polymerization of the alkaline metal salt of the 3-morpholinone with a chloromethylated vinylaryl polymer results in the incorporation of the 3-morpholinone ring structure in the resulting polymeric derivative.

U.S. Pat. No. 3,509,106 discloses a linear fiber-forming, water absorbable polyamide having ether linkages in the polymer chain. The polyamide is obtained from the polycondensation of a diamino ether with a diacid.

U.S. Pat. No. 4,064,086 discloses a fiber-forming polyamide hydrogel possessing hydroxymethyl groups in the aliphatic chain. U.S. Pat. No. 5,068,220 recognizes that the polyamide of U.S. Pat. No. 4,064,086 is bioabsorbable and is suitable for use as a surgical suture.

U.S. Pat. No. 4,126,614 discloses a 7-membered cyclic amide, referred to as a 3-oxacaprolactam, possessing a hetero oxygen atom in the ring. Polymerization of the compound provides a sticky, viscous, orange-colored material of relatively low molecular weight. Such a material is neither moldable nor extrudable and as such would not be suitable for the manufacturing of the medical devices contemplated here.

U.S. Pat. No. 4,343,931 discloses a bioabsorbable poly(esteramide) which can be employed as a surgical suture. The poly(esteramide) is prepared by reacting a diamine with lactic acid or glycolic acid to form a diamidediol, the latter then being reacted with a dicarboxylic acid to form the polymer.

U.S. Pat. No. 4,713,437 discloses a fiber-forming polyamide derived from the polycondensation of a diamine possessing one or more etheric oxygens with a dicarboxylic acid.

U.S. Pat. No. 4,855,397 discloses a polyesteramide formed by the reaction of a dicarboxylic acid possessing at least one etheric oxygen with an amino alcohol.

U.S. Pat. No. 5,051,491 discloses a fiber-forming polyamide derived from the polycondensation of a diamine and a dicarboxylic acid both of which possess one or more etheric oxygens.

U.S. Pat. Nos. 5,086,162 and 5,118,785 disclose fiber-forming, water absorbing poly(esteramides) derived from diamines possessing one or more etheric oxygens.

German Patent No. 1 195 317 discloses a process for the manufacture of a 7-membered ring compound, referred to as 1-thia-4-aza-5-oxocycloheptane, possessing an amide linkage, a hetero sulfur atom, two carbon atoms between the carbonyl of the amide linkage and the sulfur atom and two carbon atoms between the nitrogen of the amide linkage and the hetero sulfur atom. The compound is said to be useful as an intermediate product in the manufacture of pharmaceutical preparations and polycondensate plastics and as an effective inhibitor of self-oxidation processes.

SUMMARY OF THE INVENTION

In accordance with the present invention, a moldable and/or extrudable polymer is provided which possesses structural units derived from a cyclic amide of the general formula:

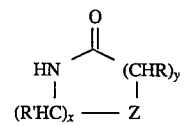

wherein Z is O, S or NR"; each of R, R' and R" individually is the same or different and is hydrogen or methyl; and, x is 1 to 5, y is 1 to 5 and the sum of x and y is at least 3.

Such monomers can be polymerized by utilizing techniques that are well known in the art, e.g., anionic polymerization using strong bases such as alkali metals, metal hydrides, metal amides, organometallic compounds, etc., or combinations of the aforementioned strong bases with acid halides and cationic polymerization using various protonic acids such as trifluoroacetic acid, toluenesulfonic acid, etc., or lewis acids such as aluminum chloride, zinc chloride, stannous octoate, and the like.

Upon polymerization, the ring structure of the cyclic amide monomer opens with subsequent condensation to form a polymer possessing oxygen, sulfur or nitrogen atoms in the polymer backbone. Such atoms increase the hydrophilicity and diminish the crystallinity of the resulting polymer. It is also within the scope of the present invention to form graft or random copolymers with such cyclic amides and one or more other monomers copolymerizable therewith.

With increasing cyclic amide monomer content, the polymer of this invention can be made to exhibit still higher rates of bioabsorbability. Since the polymers are moldable and/or extrudable, they can be used in the fabrication of a wide variety of surgical devices intended to be implanted in the body, e.g., staples, clips, sutures, pins, screws, anastomosis rings, prosthetic devices, hernial repair meshes, growth matrices, drug delivery devices, etc., including those that are intended to be bioabsorbable.

DETAILED DESCRIPTION OF THE INVENTION

Figure 1A:
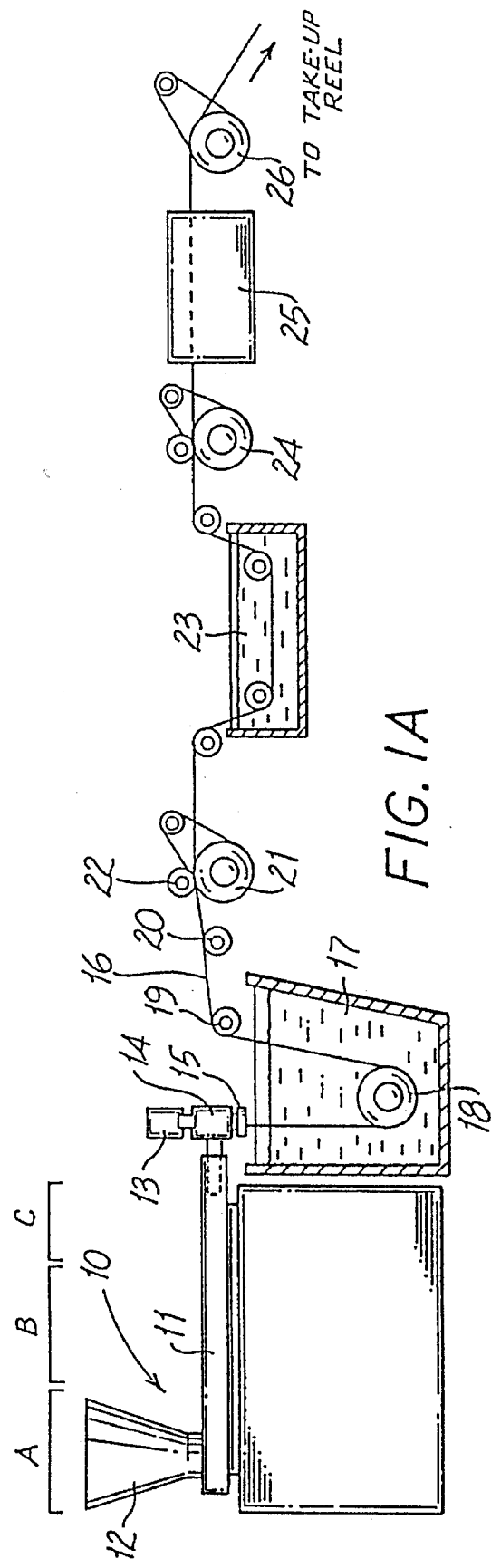
FIGS. 1A and 1B are illustrative of an extrusion process which can be used to provide a monofilament suture from the polymer of this invention.

Conventional polymerization techniques that are well known and disclosed in the prior art can be utilized in preparing the bioabsorbable polymer of the present invention. Of the cyclic amide monomers which can be used to provide the polyamides of this invention, those in which Z is oxygen are preferred. Specific monomers which can be used to provide the bioabsorbable polyamide herein include the following:

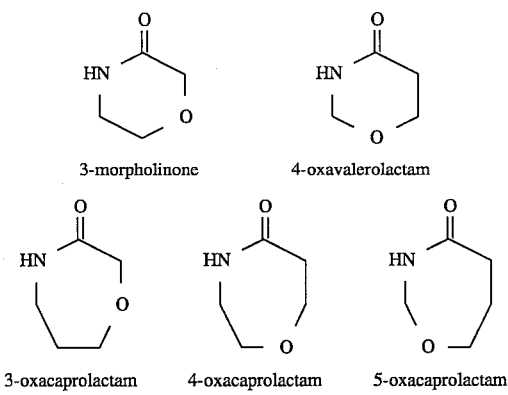

3-morpholinone     4-oxavalerolactam 3-oxacaprolactam     4-oxacaprolactam     5-oxacaprolactam Several of these hetero oxygen-containing monomers are known, i.e., 3-morpholinone which is disclosed in U.S. Pat. No. 3,133,048, supra, and 3-oxacaprolactam which is disclosed in U.S. Pat. No. 4,126,614, supra.

A variety of procedures can be used to produce the cyclic amide monomers herein. For example, ethanolamine can be reacted with ethyl chloroacetate to provide N-[2-hydroxyethyl]chloroacetamide which is thereafter cyclized to provide the known monomer 3-morpholinone.

As another example of monomer preparation, bromopropanoyl chloride can be reacted with ethanolamine to provide the novel monomer 4-oxacaprolactam.

The moldable and/or extrudable polymer of this invention comprises structural units of the formula:

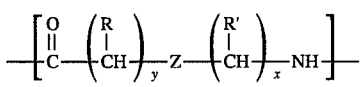

wherein Z is O, S or NR"; each of R, R' and R" individually is the same or different and is hydrogen or methyl; and, x is 1 to 5, y is 1 to 5 and the sum of x and y is at least 3.

Mixtures or sequences of two or more cyclic amide monomers of the aforesaid type can also be used herein. In addition, it is within the scope of this invention to copolymerize such monomers with one or more other monomers copolymerizable therewith such as caprolactam, ε-caprolactone, glycolide, glycolic acid, lactide, lactic acid, p-dioxanone, trimethylene carbonate, etc., to provide random or block copolymers. It is also within the scope of this invention to provide graft copolymers in which other polymer sequences are grafted on to or copolymerized with the polymer of this invention. Thus, e.g., any of various non-bioabsorbable or bioabsorbable polymers such as polyamides, polyesters, in particular, polyesters based on the polymerization or copolymerization of such monomers as glycolide, glycolic acid, lactide, lactic acid, ε-caprolactone, dioxanone, trimethylene carbonate, etc., can be grafted onto the polymers of this invention to provide copolymers exhibiting unique properties. Any of the polymers within the scope of this invention can be blended with one or more other suitable resins to provide useful moldable and/or extrudable products.

A filament useful, e.g., as a suture, can be manufactured from the polymer of this invention by methods well known in the art. A suitable process for the manufacture of a monofilament suture comprises the operations of melt extruding the polymer herein to provide a monofilament and stretching the solidified monofilament at an elevated temperature in water (or other suitable liquid medium) or in air (or other suitable gaseous medium) to provide a stretched monofilament. Optionally, the monofilament can be annealed to provide a finished suture.

FIG. 1A schematically illustrates a monofilament suture manufacturing operation which is especially suitable for producing larger size sutures, e.g., those of sizes 3/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of polymer prepared in accordance with the present invention and suitable for extrusion are introduced to the extruder through hopper 12.

Motor-driven metering pump 13 delivers melt extruded polymer at a constant rate to spin pack 14 and thereafter through a spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e. the air gap, can vary and can advantageously be from about 0.5 to about 100 cm. If desired, a chimney (not shown), or shield, can be provided to reduce the length of the air gap, e.g. to from 1 to 10 cm, thereby isolating monofilament 16 from contact with air currents which might otherwise affect the cooling of the monofilament in an unpredictable manner. Monofilament 16 is passed through quench bath 17 around driven roller 18 and over idle rollers 19 and 20. Optionally, a wiper (not shown) may remove excess water from the monofilament as it is removed from quench bath 17. On exiting the quench bath the monofilament is wrapped around a first godet 21 provided with nip roll 22 to prevent slippage which might otherwise result from the subsequent stretching operation. Monofilament 16 passing from godet 21 is stretched, to effect its orientation and thereby increase its tensile strength. In the stretching operation shown in FIG. 1A, generally suitable for larger size sutures, e.g., sizes 2 to 3/0, monofilament 16 is drawn through hot water draw bath 23 by means of second godet 24 which rotates at a higher speed than first godet 21 to provide the desired stretch ratio.

Figure 1B:
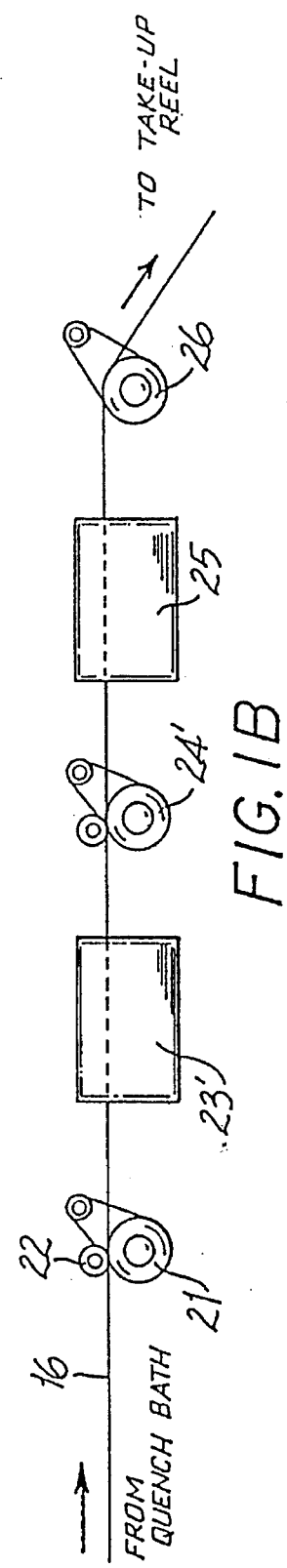

In the alternative stretching operation shown in FIG. 1B, generally preferred for smaller sutures sizes, e.g., sizes 4/0 to 8/0, monofilament 16 is drawn by second godet 24' through hot air convection oven chamber 23' to provide the desired amount of stretch. Following the stretching operation shown in FIG. 1A or 1B, monofilament 16 optionally may be subjected to an on-line annealing (relaxation) operation as a result of which the monofilament shrinks. In the process of FIGS. 1A and 1B, on line annealing with or without relaxation when desired is accomplished by driving monofilament 16 by third godet 26 through second hot air oven chamber 25. For relaxation, the Numerous other surgical articles can be manufactured from the polymer of the present invention including staples, clips, pins, hernial repair meshes and anastomosis rings. Still other surgical devices which can be made from the polymer herein include prosthetic ligaments and tendons, gauze, wound dressings, growth matrices, drug delivery devices, screws and other implants.

Drug delivery devices, as used herein, include any device or article of manufacture which is used to deliver a medicinal agent. The term "medicinal agent" is used in its broadest sense and includes any substance or mixture of substances which are useful in medicine. Thus, it is understood that a medicinal agent may be a drug, enzyme, growth factor, peptide, protein, dye, or diagnostic agent such as a releasable dye which may have no biological activity per se.

Examples of various medicinals that can be used in accordance with the present invention include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, anti-neoplastics, immunosuppressants, gastrointestinal drugs, diuretics, steroids and enzymes. It is also intended that combinations of medicinals can be used in accordance with the present invention.

The following example is illustrative of the invention.

EXAMPLE 1

The following example illustrates the preparation of the cyclic amide monomer 3-morpholinone and procedures for the polymerization of this monomer to provide a polymer in accordance with the present invention.

Ethanolamine (72 g) was dissolved in 200 ml of dioxane under nitrogen gas at room temperature. Sodium metal (23.5 g), which had been cut into small pieces, was then slowly added to the solution. The rate at which the sodium metal was added was adjusted so that hydrogen gas evolved at a gentle rate. After all the sodium metal was added, the reaction mixture was stirred at room temperature and then slowly refluxed for 3 hours until all the sodium had dissolved. The reaction mixture was cooled to room temperature and ethyl chloroacetate (150 g) was slowly added. Due to the exothermicity of this reaction, the rate at which the ethyl chloroacetate was added was controlled to maintain the temperature of the reaction below 45° C. After the addition was complete, the mixture was stirred at room temperature overnight under nitrogen gas. The solids were recovered by filtration and washed with boiling benzene and dioxane. The solutions were combined and the solvent stripped therefrom in a rotary evaporator. Needle-like crystals were obtained which were further purified by recrystalization in ether.

The polymerization of the 3-morpholinone monomer obtained by the above-described method can be carried out in glass tubes under vacuum. 3-morpholinone (5 g) is placed in a glass tube and dried under vacuum for 10 minutes. Thereafter, potassium hydride (0.02 g) is added. After drying the glass tube under vacuum briefly, the tube is sealed and placed in an oven at 75° C. for 24 hours. The tube is thereafter broken and the solid polymer is recovered.

In an alternative polymerization method, 3-morpholinone (5 g) is placed in a glass tube and dried under vacuum for 10 minutes. Thereafter, stannous octoate (0.02 g) is added. After drying the glass tube under vacuum briefly, the tube is sealed and placed in an oven at 75° C. for 24 hours. The tube is thereafter broken and the solid polymer is recovered.

What is claimed is:

1. A method of suturing a wound which comprises suturing the wound with a suture comprising: a copolymer or blend possessing structural units derived from a cyclic amid monomer of the general formula:

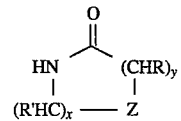

wherein Z is O, S or NR"; each of R, R' and R" individually is the same or different and is hydrogen or methyl; and x is 1 to 5, y is 1 to 5 and the sum of x and y is at least 3; and structural units derive from at least one other monomer selected from the group consisting from the group consisting from caprolactam, epislon-caprolactone, glycolide, glycolic acid, lactide, lactic acid, p-dioxanone and trimethylene carbonate.

2. The method of claim 1 wherein the suture is bioabsorbable.

* * * * *